United States Patent
Dlugos et al.

(10) Patent No.: US 8,083,665 B2
(45) Date of Patent: Dec. 27, 2011

(54) PRESSURE SENSORS FOR GASTRIC BAND AND ADJACENT TISSUE

(75) Inventors: Daniel F. Dlugos, Middletown, OH (US); Amy L. Poeppelman, Mason, OH (US); Janna M. Burrell, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 640 days.

(21) Appl. No.: 11/682,459

(22) Filed: Mar. 6, 2007

(65) Prior Publication Data

US 2008/0221598 A1    Sep. 11, 2008

(51) Int. Cl.
*A61B 17/00* (2006.01)
*A61B 17/12* (2006.01)

(52) U.S. Cl. .......................... 600/37; 606/157

(58) Field of Classification Search ............ 600/37, 600/29–30; 606/151–158
See application file for complete search history.

(56) References Cited

U.S. PATENT DOCUMENTS

| | | | |
|---|---|---|---|
| 5,074,868 A * | 12/1991 | Kuzmak | 606/157 |
| 5,601,604 A * | 2/1997 | Vincent | 606/216 |
| 5,938,669 A | 8/1999 | Klaibar et al. | |
| 6,067,991 A | 5/2000 | Forsell | |
| 6,432,040 B1 | 8/2002 | Meah | |
| 6,450,173 B1 | 9/2002 | Forsell | |
| 6,450,946 B1 * | 9/2002 | Forsell | 600/37 |
| 6,461,292 B1 | 10/2002 | Forsell | |
| 6,470,892 B1 | 10/2002 | Forsell | |
| 6,667,725 B1 * | 12/2003 | Simons et al. | 343/895 |
| 6,855,115 B2 | 2/2005 | Fonseca et al. | |
| 7,351,240 B2 * | 4/2008 | Hassler et al. | 604/891.1 |
| 7,390,294 B2 | 6/2008 | Hassler, Jr. | |
| 7,601,162 B2 | 10/2009 | Hassler, Jr. et al. | |
| 2003/0105385 A1 | 6/2003 | Forsell | |
| 2003/0114729 A1 | 6/2003 | Forsell | |
| 2003/0136417 A1 | 7/2003 | Fonseca et al. | |
| 2004/0082867 A1 | 4/2004 | Esch et al. | |
| 2005/0070937 A1 * | 3/2005 | Jambor et al. | 606/153 |
| 2006/0089571 A1 * | 4/2006 | Gertner | 600/593 |
| 2006/0173238 A1 | 8/2006 | Sung et al. | |
| 2006/0189888 A1 | 8/2006 | Hassler, Jr. et al. | |

(Continued)

FOREIGN PATENT DOCUMENTS

EP    1 736 123    12/2006

(Continued)

OTHER PUBLICATIONS

European Search Report dated Jul. 18, 2008 for Application No. 08250745.

European Search Report dated Oct. 28, 2008 for Application No. 08250745.

(Continued)

*Primary Examiner* — Charles A Marmor, II
*Assistant Examiner* — Catherine E Burk
(74) *Attorney, Agent, or Firm* — Dean L. Garner (57) ABSTRACT

An apparatus for providing a restriction and sensing an associated operational parameter, comprises a restriction device and a sensing device. The restriction device is configured to be secured around a portion of an anatomical structure. The restriction device is operable to form a restriction within the anatomical structure. The sensing device is configured to sense a parameter associated with operation of the restriction device. At least a portion of the sensing device is configured to be positioned adjacent to tissue of the anatomical structure. The restriction device may comprise a gastric band, among other things. The sensing device may comprise a pressure sensor, among other things.

12 Claims, 8 Drawing Sheets

U.S. PATENT DOCUMENTS

| | | | |
|---|---|---|---|
| 2006/0199997 A1 | 9/2006 | Hassler et al. | |
| 2006/0211913 A1 | 9/2006 | Dlugos et al. | |
| 2006/0235448 A1 | 10/2006 | Roslin et al. | |
| 2006/0247722 A1* | 11/2006 | Maschino et al. | 607/40 |
| 2007/0167672 A1 | 7/2007 | Dlugos et al. | |
| 2008/0172072 A1 | 7/2008 | Pool et al. | |
| 2008/0250340 A1 | 10/2008 | Dlugos et al. | |

FOREIGN PATENT DOCUMENTS

| | | |
|---|---|---|
| WO | WO 01/12078 | 2/2001 |
| WO | WO 03/061504 | 7/2003 |
| WO | WO 2009/050709 | 4/2009 |

OTHER PUBLICATIONS

U.S. Appl. No. 11/065,410, filed Feb. 24, 2005, Hassler et al.
U.S. Appl. No. 11/369,531, filed Mar. 7, 2006, Dlugos, Jr. et al.
U.S. Appl. No. 11/398,940, filed Apr. 4, 2006, Hassler et al.
US Patent Office Action, U.S. Appl. No. 11/369,531, dated Jan. 18, 2008, pp. 1-8.
Chinese Office Action dated Oct. 13, 2010 for Application No. 200810083304.3.
International Search Report and Written Opinion dated Apr. 27, 2011 for Application No. PCT/US2010/059051.

* cited by examiner

PRESSURE SENSORS FOR GASTRIC BAND AND ADJACENT TISSUE

BACKGROUND

Many devices and methods for treating obesity have been made and used, including but not limited to adjustable gastric bands. An example of such an adjustable gastric band is disclosed in U.S. Pat. No. 6,067,991, entitled "Mechanical Food Intake Restriction Device," which issued on May 30, 2000, and which is incorporated herein by reference. To the extent that an adjustable gastric band system is fluid based, those of ordinary skill in the art will appreciate that it may be advantageous to acquire data indicating the pressure of fluid in the band system.

Various devices and techniques for pressure data acquisition and processing for gastric band systems are disclosed in U.S. Non-Provisional application Ser. No. 11/065,410, filed Feb. 24, 2005, entitled "Device for Non-Invasive Measurement of Fluid Pressure in an Adjustable Restriction Device," and published as U.S. Pub. No. 2006/0189888; U.S. Non-Provisional application Ser. No. 11/369,531, filed Mar. 7, 2006, entitled "Non-Invasive Pressure Measurement in a Fluid Adjustable Restrictive Device," and published as U.S. Pub. No. 2006/0211913; and U.S. Non-Provisional application Ser. No. 11/398,940, filed Apr. 6, 2006, entitled "Monitoring of a Food Intake Restriction Device," and published as U.S. Pub. No. 2006/0199997. The disclosure of each of those applications and publications is incorporated by reference herein.

Similar advantages may be achieved with data indicating the pressure at or near the tissue interface of a gastric band system or other restriction device. Such pressure data may be obtained before, during, and/or after pressure adjustment, and may be useful for adjustment, diagnostic, monitoring, or other purposes. The foregoing examples are merely illustrative and not exhaustive. While a variety of techniques and devices have been used to treat obesity, it is believed that no one prior to the inventors has previously made or used an invention as described in the appended claims.

BRIEF DESCRIPTION OF THE FIGURES

While the specification concludes with claims which particularly point out and distinctly claim the invention, it is believed the present invention will be better understood from the following description of certain examples taken in conjunction with the accompanying drawings, in which like reference numerals identify the same elements and in which:

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

Figure 1:
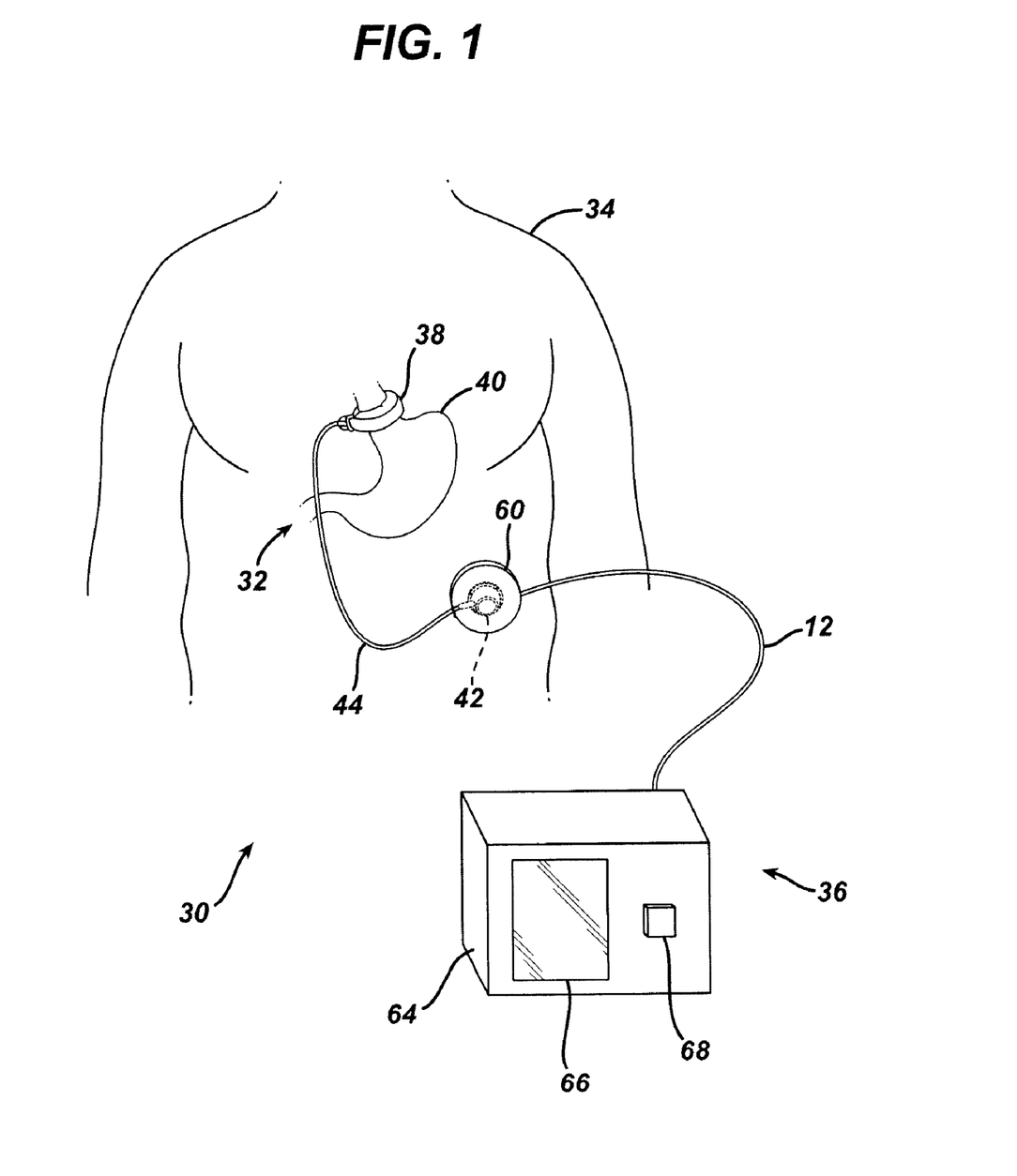
FIG. 1 is a schematic illustration of an exemplary food intake restriction system.

Referring now to the drawings in detail, wherein like numerals indicate the same elements throughout the views, FIG. 1 illustrates a food intake restriction system 30. System 30 comprises a first portion, identified generally as 32, implanted inside of a patient 34, and a second portion, identified generally as 36, located external to the patient. Implanted portion 32 comprises an adjustable gastric band 38 positioned on the upper portion of the patient's stomach 40. Adjustable band 38 may include a cavity made of silicone rubber, or another type of biocompatible material, that inflates inwardly against stomach 40 when filled with a fluid. Alternatively, band 38 may comprise a mechanically adjustable device having a fluid cavity that experiences pressure changes with band adjustments, or a combination hydraulic/mechanical adjustable band. In the present example, an injection port 42, which will be described in greater detail below, is implanted in a body region accessible for needle injections and/or telemetry communication signals. In the embodiment shown, injection port 42 fluidly communicates with adjustable band 38 via a catheter 44. A surgeon may position and permanently implant injection port 42 inside the body of the patient in order to perform adjustments of the food intake restriction or stoma created by adjustable band 38. The surgeon, for example, may implant injection port 42 in the lateral, subcostal region of the patient's abdomen under the skin and layers of fatty tissue. The surgeon may also implant injection port 42 on the sternum of the patient. Of course, any other suitable implantation sites may be used.

Figure 2:
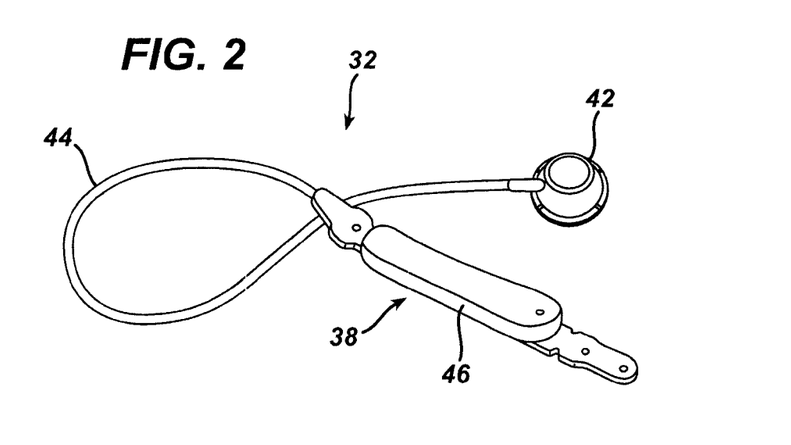
FIG. 2 is a more detailed perspective view of an exemplary implantable portion for the food intake restriction system of FIG. 1.

FIG. 2 illustrates an exemplary adjustable gastric band 38 in greater detail. In this embodiment, band 38 includes a variable volume bladder 46 that expands or contracts against the outer wall of the stomach 40 to form an adjustable stoma for controllably restricting food intake into the stomach 40. A physician may decrease the size of the stoma opening by adding fluid to variable volume bladder 46 or, alternatively, may increase the stoma size by withdrawing fluid from the bladder 46. Fluid may be added or withdrawn by inserting a needle into injection port 42. Alternatively, fluid may be transferred in a non-invasive manner between band 38 and injection port 42 using telemetry command signals. The fluid may be, but is not restricted to, a 0.9 percent saline solution.

Figure 3:
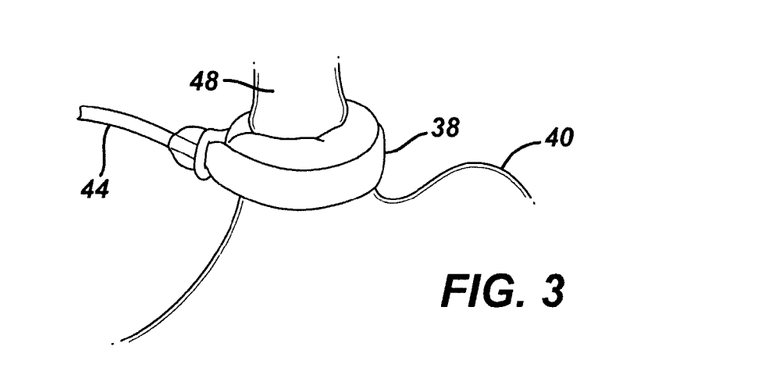
FIG. 3 is a perspective view of the adjustable gastric band of FIG. 2, showing the band positioned around the gastro-esophageal junction of a patient in an exemplary use.
Figure 4:
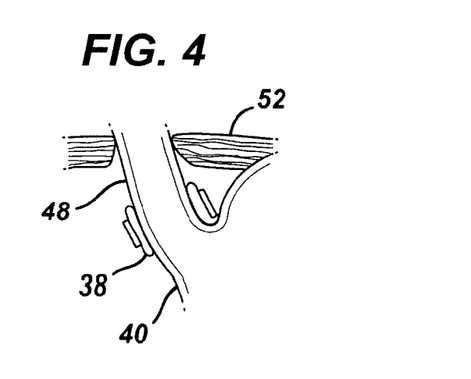
FIG. 4 is a cross-sectional view of the adjustable gastric band of FIG. 2, shown in an exemplary deflated configuration.
Figure 5:
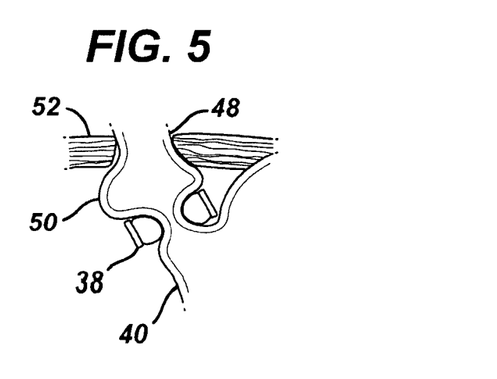
FIG. 5 is a cross-sectional view of the adjustable gastric band of FIG. 2, shown in an exemplary inflated configuration to create a food intake restriction.

FIG. 3 shows the adjustable gastric band 38 of FIG. 2 applied about the gastro-esophageal junction of a patient 34 in an exemplary use. As shown in FIG. 3, band 38 at least substantially encloses the upper portion of stomach 40 near the junction with esophagus 48. FIG. 4 is a sectional view of band 38, showing the band 38 in a deflated configuration. In this view, band 38 contains little to no fluid, thereby maximizing the size of the stoma opening into stomach 40. FIG. 5 is a cross-sectional view of band 38 and stomach 40, similar to FIG. 4, showing band 38 in an inflated, fluid-filled configuration. In this view, the pressure of band 38 against stomach 40 is increased due to the fluid within band 38, thereby decreasing the stoma opening to create a food intake restriction. FIG. 5 also schematically illustrates band 38 constricted around stomach 40 to form an upper pouch beneath the junction of stomach 40 and esophagus 48, also beneath the diaphragm muscle 52 of the patient.

Returning now to FIG. 1, external portion 36 of food restriction system 30 comprises a pressure-reading device 60 electrically connected (in this embodiment, via an electrical cable assembly 62) to a control box 64. Control box 64 includes a display 66, one or more control switches 68, and an external control module, which will be explained in further detail below. Control box 64 may be configured for use, for example, in a physician's office or examination room. Some ways to mount control box 64 include placement upon a desktop, attachment to an examination table, or hanging on a portable stand. Control box 64 may also be configured for carrying in the physician's lab coat pocket, holding by hand, or placing upon the examination table or the reclining patient. Electrical cable assembly 62 may be detachably connected to control box 64 or pressure-reading device 60 to facilitate cleaning, maintenance, usage, and storage of external portion 36 of system 30.

Pressure-reading device 60 may non-invasively measure the pressure of the fluid within implanted portion 32 even when injection port 42 is implanted beneath thick (e.g., at least over 10 centimeters, etc.) subcutaneous fat tissue. For instance, implanted portion 32 may comprise one or more pressure sensors, and pressure-reading device 60 may be configured to obtain pressure data from implanted portion 32 via telemetry or other means. To the extent that implanted portion 32 requires power from an external source, pressure-reading device 60 or some other component, may be further configured to provide transcutaneous energy transfer (TET) to implanted portion. In the present example, a physician may hold pressure-reading device 60 against the patient's skin near the location of injection port 42 in the patient and observe the pressure reading on display 66 of control box 64. Pressure-reading device 60 may also be removably attached to the patient 34, such as during a prolonged examination, using straps, adhesives, and other well-known methods. Pressure-reading device 60 operates through conventional cloth or paper surgical drapes, and may also include a disposal cover (not shown) that may be replaced for each patient.

It will be appreciated that one or more pressure sensors may be incorporated into implanted portion 32 in a variety of ways. Several structures and techniques for incorporating one or more pressure sensors into implanted portion 32 are disclosed in U.S. Non-Provisional application Ser. No. 11/369, 531, filed Mar. 7, 2006, entitled "Non-Invasive Pressure Measurement in a Fluid Adjustable Restrictive Device," and published as U.S. Pub. No. 2006/0211913, which has been incorporated by reference herein. Several additional non-exhaustive pressure sensor embodiments suitable for incorporation into or use with implanted portion 32 are illustrated in FIGS. 6-19. While the following embodiments will be discussed in the context of use with implanted portion 32, it will be appreciated that the same embodiments and variations thereof may alternatively be used with different types of implanted devices, or even in the absence of any other type of implanted device.

Figure 6:
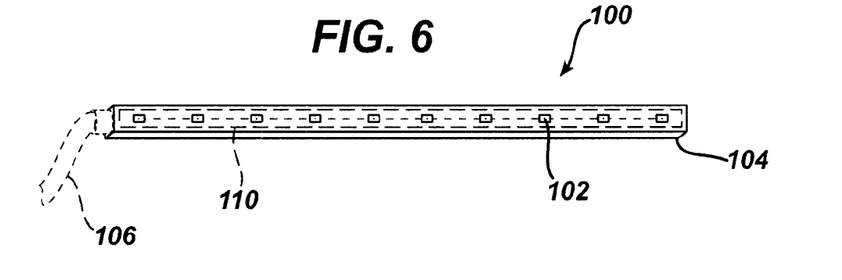
FIG. 6 is a plan view of an exemplary pressure sensing strip that may be used with the adjustable gastric band of FIG. 2.

As shown in FIG. 6, an exemplary pressure sensing strip 100 comprises a plurality of individual pressure sensors 102 on a flexible substrate 104. Each of the pressure sensors 102 is operable to sense pressure, such as by converting a physical deflection into an electrical signal, and thereby provide pressure data. Pressure sensors 102 may comprise any suitable type(s) of pressure sensors, including but not limited to piezoresistive, capacitive, strain gauges, or any other suitable sensor type, including combinations thereof. Each of the pressure sensors 102 is in communication with a flexible cable 106, which is operable to transmit data indicative of pressure sensed by pressure sensors 102. While ten pressure sensors 102 are shown in FIG. 6, it will be appreciated that any suitable number of pressure sensors 102 may be used in any suitable arrangement.

In the present example, pressure sensing strip 100 is configured to fit between a gastric band 38 and a patient's stomach 40. Pressure sensing strip 100 may thus be used to sense pressure at the tissue interface of the stomach 40 and gastric band 38. Pressure sensing strip 100 may be oriented such that pressure sensors 102 face stomach 40 or gastric band 38. Alternatively, pressure sensors 102 may be provided on both sides of pressure sensing strip 100. While pressure sensing strip 100 is shown as being generally flat, pressure sensing strip 100 may be formed such that it is pre-curved to wrap around tissue of an anatomical structure (e.g., a stomach 40, etc.) and adhere with slight preload pressure on the tissue. Pressure sensing strip 100 may thus be held in place by its own resilient properties. Alternatively, a gastric band 38 or other device may provide sufficient tension to hold pressure sensing strip 100 in place adjacent to tissue. As yet another alternative, pressure sensing strip 100 may comprise one or more features configured to maintain a position of pressure sensing strip 100 relative to tissue. For instance, a flexible biocompatible adhesive may be applied to pressure sensing strip 100, or pressure sensing strip 100 may comprise a fastener or other manipulatable feature (e.g., buckle, tensioning means, etc.) operable to secure positioning of pressure sensing strip 100.

In another embodiment (not depicted), pressure sensing strip 100 is provided within gastric band 38. By way of example only, pressure sensing strip 100 may be positioned within bladder 46 of gastric band 38. For instance, pressure sensing strip 100 may be positioned such that pressure sensors 102 face the inner wall of bladder 46, opposite stomach 40 or esophagus 48. In such a position, pressure sensing strip 100 may be configured to sense the pressure at the interface of gastric band 38 and stomach 40 or esophagus 48, or to sense some other parameter. Other suitable locations and configurations for pressure sensing strip 100 will be apparent to those of ordinary skill in the art.

In the present example, pressure data is communicated from pressure sensors 102 via cable 106 to a transmitter (not shown). The transmitter is operable to further communicate the pressure data wirelessly to a receiver (e.g., pressure-reading device 60, etc.) external to the patient 34. For instance, the transmitter may comprise one or more RF coils operable to provide telemetry with receiver coils located external to the patient 34. Similarly, to the extent that pressure sensors 102 require power from an external source for operation, the RF coils used to provide telemetry may also be used to provide transcutaneous energy transfer (TET) via cable 106 or otherwise. Alternatively, a dedicated set of TET coils may be provided. In another embodiment, a battery or other internal power source is provided in the transmitter, pressure sensing strip 100, or elsewhere. In any event, a transmitter, TET coils, a battery, and/or any other component in communication with cable 106 may be located within port 42 or elsewhere. To the extent that such components are located within or near port 42, cable 106 may be positioned alongside catheter 44.

In another embodiment, a pressure sensing strip is provided without cable 106. In this embodiment, a coil 110 is provided within pressure sensing strip 100. Each pressure sensor 102 is in communication with coil 110. As with the telemetry and TET coils discussed above, coil 110 may be operable to provide telemetry and/or TET with an external device such as pressure-reading device 60. Alternatively, separate coils 110 within pressure sensing strip 100 may be used—one for telemetry and one for TET. In yet another embodiment, one or more coils are provided within pressure sensing strip 100 while one or more other coils are provided elsewhere (e.g., within port 42, etc.). Other suitable configurations will be apparent to those of ordinary skill in the art.

It will be appreciated that pressure sensors 102 may be un-powered or passive. For instance, a pressure sensor 102 may be configured to reflect a signal transmitted from an external transmitter such as a telemetry coil. The reflected signal may then be read and demodulated or decoded by the transmitter device or by some other receiver. The reflected signal may indicate a parameter (e.g., pressure, etc.) sensed by a sensor. By way of example only, each pressure sensor 102 may comprise a sensor such as any of the sensors described in U.S. Pat. No. 6,855,115, issued Feb. 15, 2005, and entitled "Implantable Wireless Sensor for Pressure Measurement within the Heart;" U.S. Pub. No. 2003/0136417, published Jul. 24, 2003, and entitled "Implantable Wireless Sensor;" and/or WO 03/061504, published Jul. 31, 2003, and entitled "Implantable Wireless Sensor." The disclosure of each of U.S. Pat. No. 6,855,115; U.S. Pub. No. 2003/0136417; and WO 03/061504 is incorporated by reference herein. Of course, any of the transmitters or receivers described in those references may also be used. It will also be appreciated that each sensor may be configured to provide a unique reflected signal or signature that distinguishes each sensor from other sensors. Such unique signals or signatures may permit a pressure profile to be generated. Other ways of providing a wireless, passive, and/or reflective sensor will be apparent to those of ordinary skill in the art.

Figure 7:
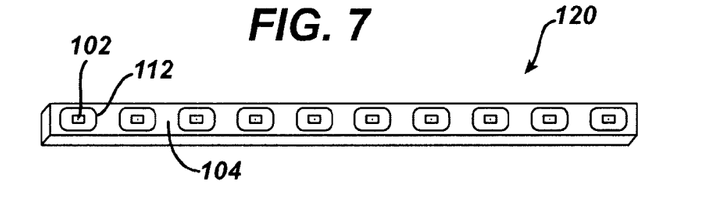
FIG. 7 is a plan view of an exemplary alternative pressure sensing strip that may be used with the adjustable gastric band of FIG. 2.

In still another embodiment, an example of which is depicted in FIG. 7, a pressure sensing strip 120 comprises a plurality of pressure sensors 102, and each pressure sensor 102 has a respective discrete coil 112. As with the version having coil 110 within pressure sensing strip 100, each coil 112 of this example may be provided within pressure sensing strip 102, and each coil 112 may be operable to provide telemetry and/or TET with an external device such as pressure-reading device 60. Furthermore, where coils 112 are provided within pressure sensing strip 120, cable 106 need not necessarily be present.

While the foregoing examples of pressure sensing strips 100, 120 include an arrangement of pressure sensors 102 along a substantially straight line, it will be appreciated that pressure sensors 102 may be provided in any suitable alternative arrangement. For instance, in the pressure strip 121 shown in FIG. 8, a plurality of pressure sensors 102 are provided in an array that covers a broader area than would otherwise be covered if pressure sensors 102 were arranged in a straight line. In this embodiment, flexible strip 105 of pressure sensing strip 121 is relatively wider than flexible strip 104 of pressure sensing strips 100, 120. Other suitable arrangements of pressure sensors 102 will be apparent to those of ordinary skill in the art, as will factors that may affect decisions regarding arrangements of pressure sensors 102, and structural variations of flexible strips 104, 105 that may be used to accommodate or compliment such alternative arrangements of pressure sensors 102.

Figure 8:
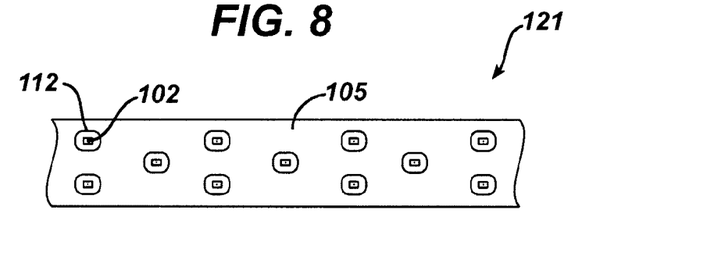
FIG. 8 is a plan view of another exemplary alternative pressure sensing strip that may be used with the adjustable gastric band of FIG. 2.
Figure 9:
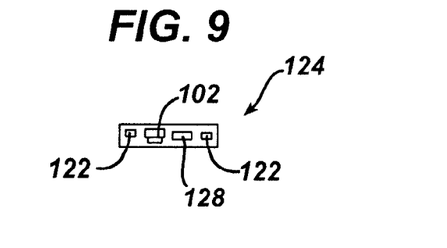
FIG. 9 is a cross-sectional view of an exemplary sensing element that may be used with the pressure sensing strips of FIGS. 7-8.

In a variation of the embodiments depicted in FIGS. 7-8, each pressure sensor 102 is provided within a respective pressure sensing module 124 having integrated electronics. In particular, and as shown in FIG. 9, each pressure sensing module 124 comprises a pressure sensor 102, a coil 122, and an application-specific integrated circuit (ASIC) 128. Such components may be in communication with one another in any suitable fashion. Each pressure sensing module 124 may be incorporated into a flexible strip 104, 105 in a manner similar to pressure sensors 102 being incorporated into flexible strips 104, 105 in the embodiments depicted in FIGS. 7-8.

While the embodiment depicted in FIG. 9 shows an ASIC 128 within each pressure sensing module 124 having a single associated pressure sensor 102, it will be appreciated that a single ASIC 128 may be in communication with a plurality of pressure sensors 102. For instance, an ASIC 128 may be configured to multiplex or scan data from a plurality of pressure sensors 102. Such an ASIC 128 may be provided on or in a sensing strip 100, 120, 121, such as in a module (not shown) that is separate from but in communication with pressure sensors 102. An ASIC 128 may also be provided as part of an individual pressure sensor 102. Still other ways in which an ASIC 128 or similar device may be incorporated into a pressure sensing strip 100, 120, 121, and other suitable relationships between one or more ASIC's 128 and one or more pressure sensors 102, will be apparent to those of ordinary skill in the art.

Figure 10:
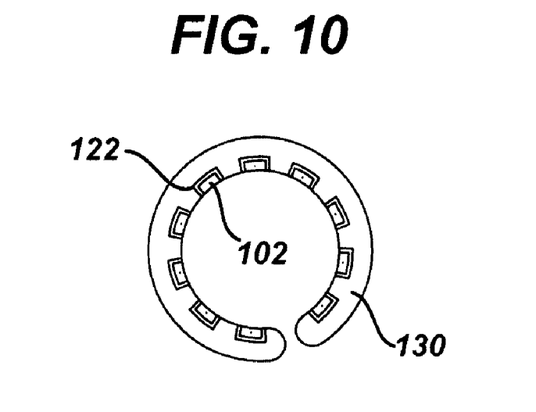
FIG. 10 is a plan view of an exemplary tissue interface member with integral pressure sensors.
Figure 11:
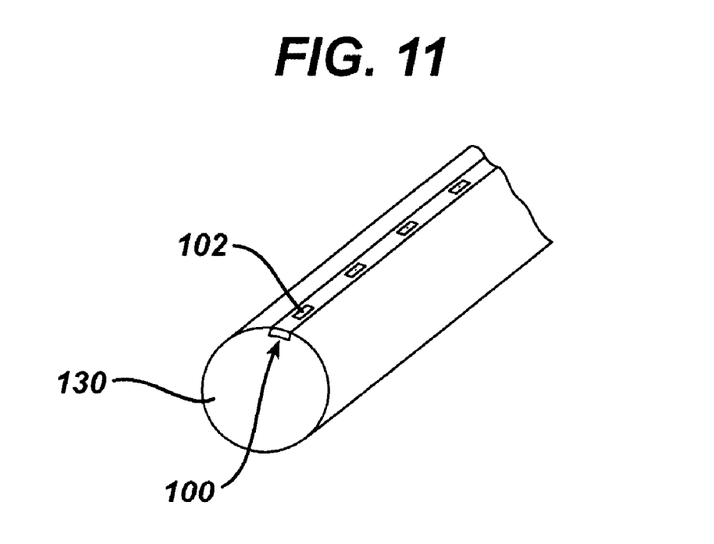
FIG. 11 is a partial perspective view of an exemplary tissue interface member with an integral pressure sensing strip.

In lieu of being provided on a pressure sensing strip 100, 120, 121, pressure sensors 102 may be provided integrally within a tissue interface member 130 of any suitable medical device. An example of pressure sensors 102 with corresponding discrete coils 122 being provided integrally within a tissue interface member 130 is shown in FIG. 10. By way of example only, tissue interface member 130 may be part of a gastric band 38, such as a bladder 46 of a gastric band. Alternatively, and as shown in FIG. 11, a pressure sensing strip 100 may be provided integrally within a tissue interface member 130. Of course, any other type of pressure sensing strip 120, 121 may also be provided integrally within a tissue interface member 130. Other suitable ways in which a plurality of pressure sensors 102 may be incorporated with or otherwise used with a tissue interface member 130, with or without any associated pressure sensing strip 100, 120, 121, will be apparent to those of ordinary skill in the art.

In view of the foregoing, it will be appreciated that the pressure sensors 102 of the embodiments depicted in FIGS. 6-11 (among other embodiments) may be used to obtain discrete pressure measurements around tissue adjacent to such pressure sensors 102. Pressure sensors 102 may be configured such that each pressure measurement may be associated with a particular pressure sensor 102, which may permit association of pressure measurements with particular tissue locations. For instance, being able to associate pressure measurements with particular tissue locations may permit a user to determine whether there is too much or too little pressure against a particular tissue location. Similarly, discrete pressure measurements may be used to identify points of tissue erosion, to detect migration of gastric band 38, or for other purposes.

Furthermore, to the extent that discrete pressure measurements may be obtained using a plurality of pressure sensors 102, a pressure profile may be generated. For instance, a pressure profile may correlate a given pressure measurement with a particular sensor, and therefore with a particular location on a gastric band 38 and/or stomach 40. Similarly, a pressure profile may be used to establish how pressure is allocated along the length or circumference of the interface of a gastric band 38 and stomach 40. It will also be appreciated that discrete pressure measurements and/or a pressure profile may be geometrically reconstructed to show the relative shape and/or size of food being swallowed by a patient, or for other purposes. Other ways in which a pressure profile may be established and/or used will be apparent to those of ordinary skill in the art.

Suitable structures or techniques for correlating a pressure measurement with a particular pressure sensor 102 will be apparent to those of ordinary skill in the art. In one embodiment, each pressure sensor 102 has an associated identification code, which may be transmitted with pressure data obtained with the corresponding pressure sensor 102. Alternatively, each pressure sensor 102 may be associated with a dedicated data interface port (not shown), and each such port may transmit or otherwise be associated with a unique identification code. In another variation, as discussed above, each pressure sensor 102 may be configured to provide a unique reflected signal or signature that distinguishes each sensor 102 from other sensors 102.

As another variation, pressure measurements may be averaged, compared, or otherwise combined by a local component (e.g., an ASIC, etc.) on a pressure sensing strip 100, 120, 121, such that a pressure value communicated externally is not associated with a particular pressure sensor 102. Of course, some other component (e.g., an external component, etc.) may also average, compare, or otherwise combine pressure measurements. Other ways in which discrete or averaged pressure measurements may be obtained, communicated, handled, and used will be apparent to those of ordinary skill in the art.

Figure 12:
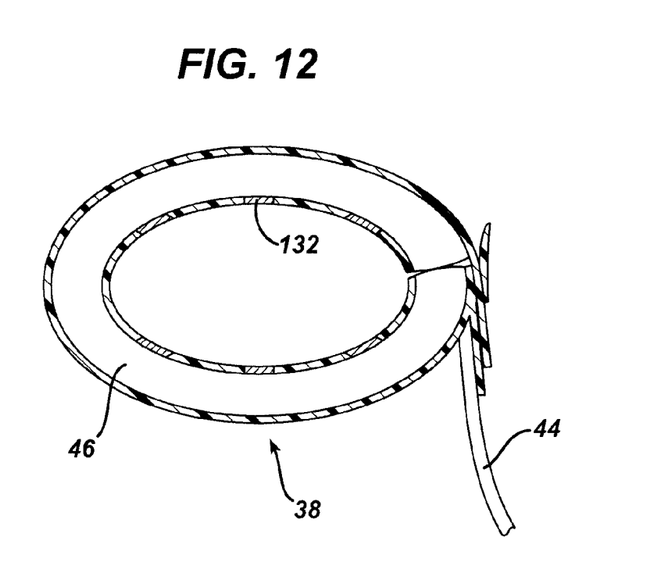
FIG. 12 is a cross-sectional view of an exemplary gastric band with strain gauges molded into an inflatable portion.
Figure 13:
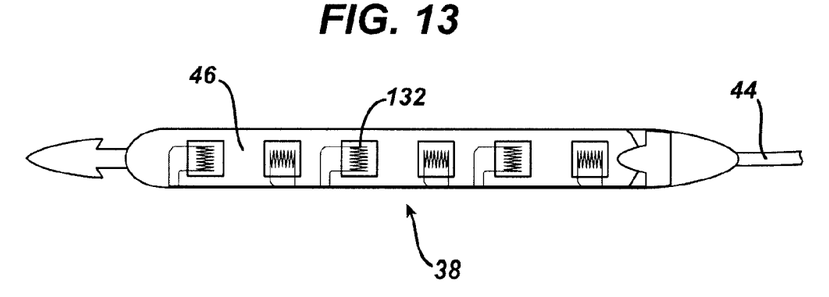
FIG. 13 is a plan view of the gastric band of FIG. 12 in an unwrapped configuration.

In another embodiment, an example of which is shown in FIGS. 12-13, a plurality of strain gauges 132 are molded into the wall of a silicon bladder 46 of a gastric band 38. Each of the strain gauges 132 is operable to sense strain within the wall of bladder 46. As shown, strain gauges 132 are arranged such that their patterns are in orientations alternating between horizontal and vertical. Alternatively, any other suitable orientations for strain gauges 132 may be used. Furthermore, while strain gauges 132 are shown as being placed along the length of silicon bladder 46, strain gauges 132 may also be placed along the radius of silicon bladder 46 or in any other suitable arrangement.

Strain gauges 132 may comprise any suitable type of strain gauge 132, including but not limited to a foil type, piezoresistor semiconductor, or any other type. In another embodiment, bladder 46 comprises a polyimide flexible sensory skin, which is itself operable to detect strain. Alternatively, any suitable type of pressure sensor 102 or other type of strain gauge 132 may be substituted for, or used to supplement, strain gauges 132 of the present example. Other suitable types of strain gauges 132 or features operable to detect strain or similar parameters will be apparent to those of ordinary skill in the art.

In the present example, it will be appreciated that strain of bladder 46 measured by strain gauges 132 may be used in a manner similar to pressure measured using any of the various pressure sensors described herein. That is, strain levels measured using strain gauges 132 may be used as feedback before, during, and/or after adjustment of gastric band 38 to achieve ideal operating conditions of gastric band 38. For instance, strain measured using strain gauges 132 may be indicative of the manner in which a gastric band 38 is interacting with tissue, how full the gastric band 38 is, etc. Alternatively, strain gauges 132 may be used for any other suitable purpose. Also similar to the various pressure sensors described herein, power may be communicated to strain gauges 132 in any suitable manner, and data may be communicated from strain gauges in any suitable manner, including but not limited to using the TET, telemetry, and/or passive technologies described herein.

Figure 14:
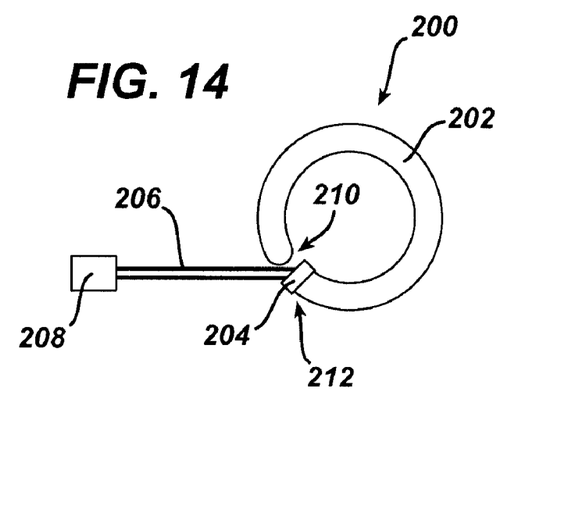
FIG. 14 is a plan view of an exemplary pressure sensing bladder system.
Figure 15:
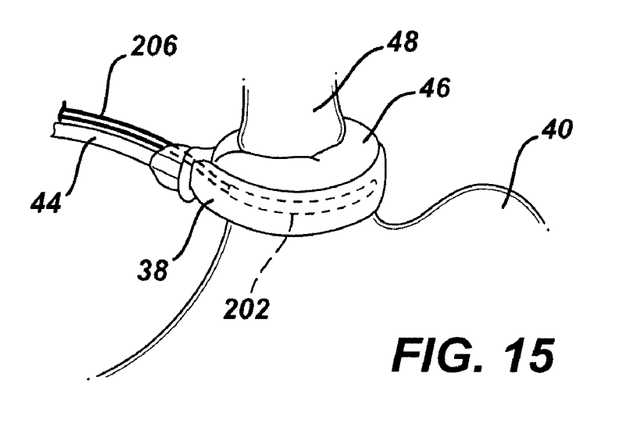
FIG. 15 is a partial perspective view of a gastric band and the pressure sensing bladder system of FIG. 14 positioned around the gastro-esophageal junction of a patient in an exemplary use.
Figure 16:
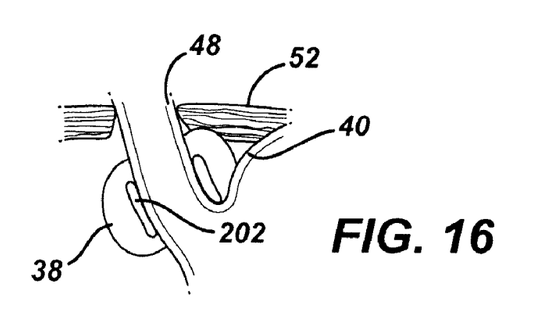
FIG. 16 is a cross-sectional view of the gastric band and pressure sensing bladder system of FIG. 15.

In another set of embodiments, a separate bladder is used to communicate pressure to a sensor. By way of example only, as shown in FIGS. 14-16, a pressure sensing device 200 comprises a pressure bladder 202, a pressure sensor 204, a cable 206, and an interface module 208. Pressure sensing device 200 may be used in combination with a gastric band 38, as shown in FIGS. 15-16, or in any other setting. While a fluid-filled gastric band 38 is shown, it will be appreciated that pressure sensing device 200 may be used with any other type of gastric band, including but not limited to a mechanical gastric band. Alternatively, pressure sensing device 200 may be used with another implanted device or by itself (i.e. not in conjunction with use of another device). Pressure bladder 202 of the present example comprises a flexible tube, which may be filled with any suitable fluid or substance, including but not limited to water, saline, silicon oil, gel, etc. To the extent that pressure sensing device 200 is used with a gastric band 38, pressure bladder 202 may be sized according to the maximum diameter of gastric band 38 or based on any other considerations. For instance, bladder may have a relatively thin cross section or diameter. Pressure bladder 202 may also be configured such that it may conform to any adjustments made to gastric band 38.

Pressure bladder 202 of this example has a free end 210 and a coupled end 212. Pressure sensor 204 is located at coupled end 212, and is operable to sense pressure of fluid or any other medium within pressure bladder 202. Cable 206 is coupled with coupled end 212 of pressure bladder 202, and is in communication with pressure sensor 204. Interface module 208 is also in communication with cable 206. In one embodiment where pressure sensing device 200 is used with a port-based gastric band 38 system, interface module 208 is positioned within or adjacent to injection port 42. Alternatively, any other suitable location for interface module 208 may be used.

In view of the above, it will be appreciated that measurements of the pressure of fluid within pressure bladder 202 may be obtained using pressure sensor 204, and may be communicated to interface module 208 via cable 206. Interface module 208 may be operable to communicate such pressure measurements to an external receiver using any suitable structures and techniques, including but not limited to telemetry with pressure-reading device 60. Similarly, to the extent that pressure sensor 204 requires power to operate, such power may be provided by or via interface module 208. For instance, interface module 208 may comprise a battery or other energy storage device, or interface module 208 may be configured to receive TET signals from an external source such as pressure-reading device 60. Still other ways in which power may be provided to pressure sensing device 200, and other ways in which data may be communicated from pressure sensing device 200, will be apparent to those of ordinary skill in the art.

In an exemplary use, illustrated in FIGS. 15 and 16, pressure sensing device 200 is positioned around the gastro-esophageal junction of a patient 34. A gastric band 38 is then applied around the pressure sensing device 200 at the gastro-esophageal junction of the patient 34. As fluid is added to gastric band 38, pressure experienced by bladder 202 increases, and such pressure is communicated to pressure sensor 204 via whatever medium (e.g., liquid, etc.) is in bladder 202. The pressure is sensed by pressure sensor 204 and communicated to an external device, such as pressure-reading device 60, via cable 206 and interface module 208. Pressure data so communicated may be displayed to a physician, such as via display 66, and may be used by the physician while adjusting gastric band 38. Of course, pressure sensing device 200 may be used in any other suitable way and in any other suitable context.

Figure 17:
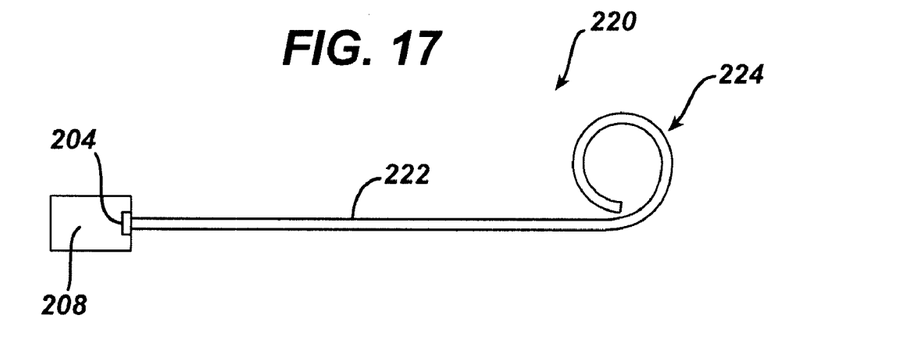
FIG. 17 is a plan view of an exemplary alternative pressure sensing bladder system, employing a single sensor and lumen.

In another embodiment, depicted in FIG. 17, a pressure sensing device 220 comprises a tube 222, a pressure sensor 204, and an interface module 208. Similar to bladder 202 discussed above, tube 222 may be filled with any suitable fluid or substance, including but not limited to water, saline, silicon oil, gel, etc. Tube 222 is flexible and has a precurved end in this example, though tube 222 may have any other properties.

With the exception of lacking cable 206, pressure sensing device 220 of FIG. 17 is similar to pressure sensing device 200 of FIGS. 14-16 in a number of ways. For instance, pressure sensing device 220 may be used with a gastric band 38, with any other implanted device, or by itself in any manner similar to such use described above with respect to pressure sensing device 200. In addition, pressure sensor 204 of pressure sensing device 220 is in communication with interface module 208 of pressure sensing device 220; and pressure sensor 204 and interface module 208 of pressure sensing device 220 may be configured and operable just like pressure sensor 204 and interface module 208 of pressure sensing device 200 as described above. Accordingly, pressure sensing device 220 may be used to sense pressure experienced between a gastric band 38 and the gastro-esophageal junction of a patient 34, and may be communicate sensed pressure to a device external to a patient (e.g., to a pressure-reading device 60 for display of pressure data on display 66, etc.).

Figure 18:
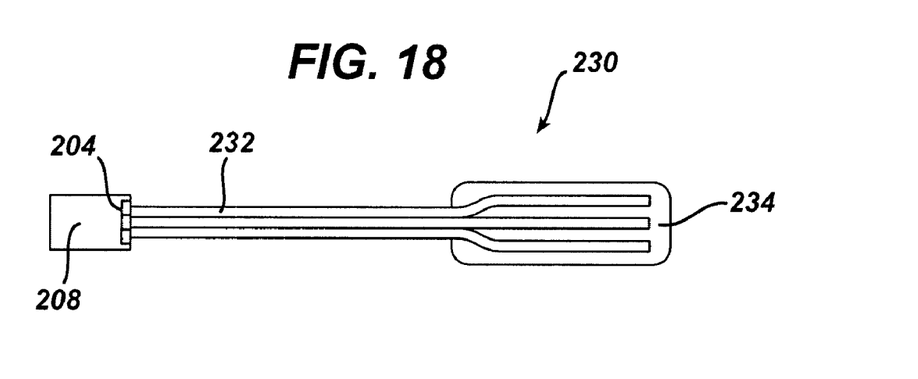
FIG. 18 is a plan view of another exemplary alternative pressure sensing bladder system, employing a plurality of sensors and lumens.
Figure 19:
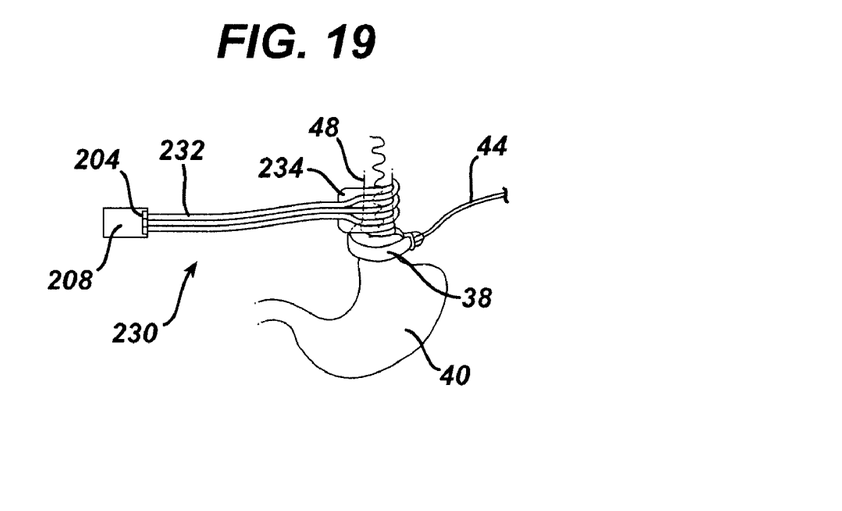
FIG. 19 is a plan view of the pressure sensing bladder system of FIG. 18 positioned near a gastric band at the gastro-esophageal junction of a patient in an exemplary use.

In an exemplary variation of pressure sensing device 220, shown in FIGS. 18-19, a pressure sensing device 230 comprises a plurality of tubes 232, a plurality of associated pressure sensors 204, and an interface module 208. The plurality of tubes 232 are secured to a flexible web 234, which is merely optional like other components described herein. Pressure sensing device 230 of FIGS. 18-19 is otherwise similar to pressure sensing device 220 of FIG. 17, and its components may therefore be configured and operable in a manner similar to the components of pressure sensing device 220 as described above.

It will also be appreciated that having a plurality of tubes 232 in pressure sensing device 230 may provide functionality that may not be available in certain embodiments of pressure sensing device 230 having a single tube 222. For instance, one tube 232 may be positioned between gastric band 38 and the gastro-esophageal junction of a patient 34, while the other two tubes 232 may be wrapped around the esophagus 48 of the patient 34. Such placement of tubes 232 may permit measurement of peristaltic parameters as a patient 34 swallows. For instance, the timing, spacing, speed, magnitude, and/or other parameters of peristaltic waves may be sensed using a plurality of tubes 232 and communicated to a device external to the patient 34. Of course, members of a plurality of tubes 232 may be positioned in any other suitable locations and arrangements for any suitable purposes. Similarly, while three tubes 232 are shown in the depicted plurality, it will be appreciated that any suitable number of tubes 232 or tube 232 substitutes may be used.

In the present example, the three tubes 232 are in fluid isolation relative to one another. In other words, fluid cannot be communicated from one tube 232 to another tube 232. However, in an alternative embodiment, a plurality of tubes 232 are in fluid communication with one another. In yet another embodiment, at least two tubes 232 of a plurality are in fluid communication with one another, while those tubes are in fluid isolation relative to another tube 232 of the plurality. Still other suitable modifications of pressure sensing devices 200, 220, 230, and alternative uses for pressure sensing devices 200, 220, 230 will be apparent to those of ordinary skill in the art.

By way of example only, in any of the foregoing embodiments, it will be appreciated that display 66 or some other device may be used to provide approximately real-time pressure measurements to a user before, during, and after the addition or withdrawal of fluid to or from implanted portion 32. For instance, a surgeon may adjust the saline content of implanted portion 32 while patient 34 swallows a fixed amount of water, and may monitor the pressure level in implanted portion 32 via display 66 during such activities. It will be appreciated that an optimal pressure adjustment may be determined based on a variety of factors related to pressure data, including but not limited to any of the following: the original baseline pressure; the new baseline pressure; the maximum peristaltic pressure; the minimum peristaltic pressure; the length of a peristaltic contraction; the Fourier transform of a peristaltic contraction data spike; the pressure decay time constant during persistaltic contractions; the total averaged pressure decay time constant during a water swallowing period; the number of peristaltic contractions to swallow a fixed amount of water; one or more forces exerted by an implanted device and/or an anatomical structure; energy of an implanted device or of fluid therein; the fill rate of fluid into an implanted device; the volume of fluid in an implanted device; the capacity of an implanted device; the flow rate of fluid into or within an implanted device; the pressure pulse rate of fluid within an implanted device; a counted number of pressure pulses of fluid within an implanted device; one or more electrical signals communicated from tissue prior to and/or in response to adjustment of an implanted device; chemical(s) output from tissue prior to and/or in response to adjustment of an implanted device; other tissue feedback responsive to adjustment of an implanted device; or any other factors.

In one embodiment, control box 64 is operable to receive data indicative of the above-noted factors in any suitable fashion (e.g., from sensors, etc.), and is further operable to automatically process such factors and present the result of such processing to the user via display 66. For instance, control box 64 may be configured to determine an ideal amount of fluid to be added or withdrawn based on such processing of factors, and may simply display a message to the user such as "Add 4 cc's of fluid," "Withdraw 0.5 cc's of fluid," or the like. Such messages may be displayed in addition to or in lieu of displaying pressure measurements, changes in pressure, or other data. Other suitable processes of any of the above-noted factors or other factors, as well as ways in which results of such processes may be presented to the user, will be apparent to those of ordinary skill in the art.

As discussed above, it may be desirable to account for temperature, atmospheric pressure, and other factors when considering measurements of pressure within or near implanted portion 32. Accordingly, pressure-reading device 60 or any other component may receive additional data such as temperature measurements taken within or near implanted portion 32, and control box 64 may comprise logic configured to adjust pressure readings in accordance with a variety of such factors.

Figure 20:
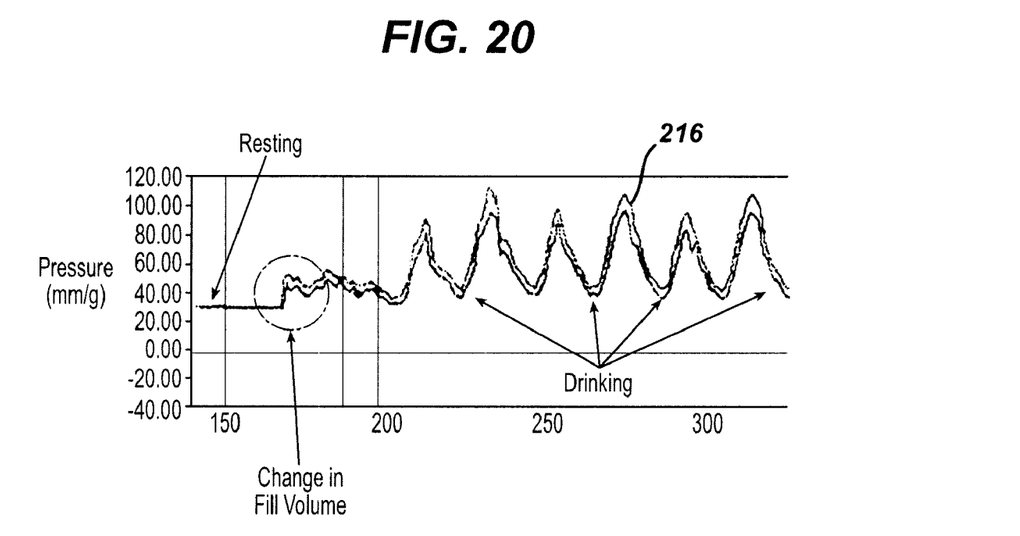
FIG. 20 is a graph indicating a pressure signal from a pressure sensing system, such as may appear on an external monitor display during interrogation by a user.

FIG. 20 is an exemplary graphical representation of a pressure signal 216 from any of the foregoing pressure sensing systems, such as may appear on display 66 during interrogation by a user. In one embodiment, the fluid pressure is initially measured by pressure reading device 60 while the patient is stable, resulting in a steady pressure reading as shown. Next, an adjustment is applied to band 38 to decrease the stoma size. During the band adjustment, the pressure sensing system continues to measure the fluid pressure and transmit the pressure readings to control box 64. As seen in the graph of FIG. 20, the pressure reading rises slightly following the band adjustment. In the example shown, the patient is then asked to drink a liquid to check the accuracy of the adjustment. As the patient drinks, the pressure sensing system continues to measure the pressure spikes due to the peristaltic pressure of swallowing the liquid, and transmit the pressure readings to external module 36 for display. By measuring and visually depicting the loading of the restriction device against the peristaltic motion of the stomach both during and after an adjustment, the system of the present example provides the physician with an accurate, real-time visualization of the patient's response to the adjustment. This instantaneous, active display of recorded pressure data enables the physician to perform more accurate band adjustments. The data may be displayed over time to provide a pressure verses time history.

In addition to use during adjustments, the pressure sensing systems of the foregoing examples may also be used to measure pressure variations in or near implanted portion 32 at various intervals during treatment. Periodic pressure readings may enable the pressure sensing system to function as a diagnostic tool, to ensure that adjustable band 38 is operating effectively. In particular, a pressure sensing system may be utilized to detect a no pressure condition within or near band 38, which may indicate a fluid leakage or other condition. Alternatively, the system may be used to detect excessive pressure spikes within or near band 38, which may indicate a kink in catheter 44 or a blockage within the stoma or other conditions.

It will become readily apparent to those skilled in the art that the above invention has equally applicability to other types of implantable bands. For example, bands are used for the treatment of fecal incontinence. One such band is described in U.S. Pat. No. 6,461,292 which is hereby incorporated herein by reference. Bands can also be used to treat urinary incontinence. One such band is described in U.S. Patent Application 2003/0105385 which is hereby incorporated herein by reference. Bands can also be used to treat heartburn and/or acid reflux. One such band is described in U.S. Pat. No. 6,470,892 which is hereby incorporated herein by reference. Bands can also be used to treat impotence. One such band is described in U.S. Patent Application 2003/0114729 which is hereby incorporated herein by reference.

The present invention has application in conventional endoscopic and open surgical instrumentation as well as application in robotic-assisted surgery.

Embodiments of the devices disclosed herein can be designed to be disposed of after a single use, or they can be designed to be used multiple times. Embodiments may, in either or both cases, be reconditioned for reuse after at least one use. Reconditioning may include any combination of the steps of disassembly of the device, followed by cleaning or replacement of particular pieces, and subsequent reassembly. In particular, embodiments of the device may be disassembled, and any number of the particular pieces or parts of the device may be selectively replaced or removed in any combination. Upon cleaning and/or replacement of particular parts, embodiments of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, embodiments described herein may be processed before surgery. First, a new or used instrument may be obtained and if necessary cleaned. The instrument may then be sterilized. In one sterilization technique, the instrument is placed in a closed an sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. the sealed container may keep the instrument sterile until it is opened in a medical facility. A device may also be sterilized using any other technique known in the art, including but not limited to beta or gamma radiation, ethylene oxide, or steam.

While the present invention has been illustrated by description of several embodiments, it is not the intention of the applicant to restrict or limit the spirit and scope of the appended claims to such detail. Numerous other variations, changes, and substitutions will occur to those skilled in the art without departing from the scope of the invention. For instance, the device and method of the present invention has been illustrated in relation to providing the pressure sensor within the injection port. Alternatively, the sensor could be positioned within a fluid filled portion of the band in order to measure pressure changes within the band. Additionally, the pressure sensor could be associated with an elastomeric balloon implanted within the stomach cavity to measure fluid pressure within the balloon. The structure of each element associated with the present invention can be alternatively described as a means for providing the function performed by the element. It will be understood that the foregoing description is provided by way of example, and that other modifications may occur to those skilled in the art without departing from the scope and spirit of the appended Claims.

What is claimed is:

1. An apparatus for providing a restriction and sensing an associated operational parameter, the apparatus comprising:
   (a) an implantable restriction device configured to be secured around a portion of an anatomical structure, wherein the implantable restriction device comprises an inflatable gastric band, wherein the restriction device is operable to form a restriction within the anatomical structure, wherein the implantable restriction device presents an inner perimeter and an outer perimeter, wherein the inner perimeter is configured to engage the anatomical structure, wherein the inner perimeter has a length extending around a corresponding circumferential length of the anatomical structure, wherein the inner perimeter defines an annular recess extending around the inner perimeter, wherein the implantable restriction device has a first end and a second end, wherein the first end defines an opening, wherein the opening is configured such that the second end is insertable through the opening of the first end, wherein the second end is operable to be drawn through the opening of the first end; and
   (b) an implantable sensing device configured to sense a parameter associated with operation of the restriction device, wherein at least a portion of the sensing device is configured to be positioned adjacent to tissue of the anatomical structure, wherein the sensing device comprises a sensor strip and a plurality of sensors, wherein the sensors are arranged in a spaced apart relationship relative to each other along at least part of the length of the inner perimeter of the implantable restriction device, such that different sensors are simultaneously positionable at different positions along the circumferential length of the anatomical structure, wherein the plurality of sensors are arranged on the sensor strip, wherein the sensor strip has a front side and a back side, wherein at least a portion of the plurality of sensors are positioned on the front side, wherein at least a portion of the plurality of sensors are positioned on the back side, wherein the sensor strip is integrated into the annular recess.

2. The apparatus of claim 1, wherein the sensor strip is configured to be positioned between the restriction device and the anatomical structure.

3. The apparatus of claim 1, wherein the plurality of sensors comprises at least one pressure sensor.

4. The apparatus of claim 1, wherein each sensor of the plurality of sensors is configured to sense the parameter associated with operation of the restriction device, wherein the plurality of sensors is configured to obtain data sufficient to establish a profile of the parameter sensed by the sensors, wherein the profile indicates allocation of the sensed parameter among the sensors.

5. The apparatus of claim 1, wherein the restriction device comprises a tissue interface portion, wherein at least a portion of the sensing device is molded within the tissue interface portion of the restriction device.

6. The apparatus of claim 1, wherein the sensing device is operable to communicate data representing a sensed parameter to a location external to a patient.

7. The apparatus of claim 6, wherein the sensing device comprises an RF coil operable to communicate data representing a sensed parameter to a location external to a patient.

8. The apparatus of claim 7, wherein the pressure sensing device further comprises a plurality of RF coils, wherein each sensor of the plurality of sensors is associated with a corresponding RF coil.

9. The apparatus of claim 1, wherein the plurality of sensors comprises at least one strain gauge.

10. The apparatus of claim 1, wherein the implantable restriction device is configured to inwardly inflate to form a restriction.

11. The apparatus of claim 1, wherein the plurality of sensors are positioned such that the plurality of sensors are positioned non-collinearly along the inner perimeter of the implantable restriction device.

12. The apparatus of claim 1, wherein the implantable restriction device is in communication with an injection port, wherein the injection port is configured to receive or remove a fluid through the injection port such that the receipt or removal of fluid is operable to control the degree of the restriction within the anatomical structure.

* * * * *